United States Patent
Feng et al.

(10) Patent No.: US 10,379,099 B2
(45) Date of Patent: Aug. 13, 2019

(54) LUBRICATION DETECTION METHOD FOR LINEAR MOTION SYSTEM

(71) Applicant: HIWIN TECHNOLOGIES CORP., Taichung (TW)

(72) Inventors: Yi-Chun Feng, Taichung (TW); Yi Hung, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 307 days.

(21) Appl. No.: 15/271,558

(22) Filed: Sep. 21, 2016

(65) Prior Publication Data

US 2018/0080889 A1    Mar. 22, 2018

(51) Int. Cl.
G01N 33/28    (2006.01)
G01N 25/72    (2006.01)
F16N 29/04    (2006.01)

(52) U.S. Cl.
CPC ............. G01N 33/28 (2013.01); F16N 29/04 (2013.01); *F16N 2200/10* (2013.01)

(58) Field of Classification Search
CPC ............................... G01N 25/72; G01N 33/28
See application file for complete search history.

(56) References Cited

U.S. PATENT DOCUMENTS

| | | | | |
|---|---|---|---|---|
| 4,527,661 A | * | 7/1985 | Johnstone | B23Q 11/121 184/6.1 |
| 4,852,693 A | * | 8/1989 | Nakajima | F16N 29/04 184/108 |
| 5,224,051 A | * | 6/1993 | Johnson | G05D 21/02 184/6.14 |
| 7,610,962 B2 | * | 11/2009 | Fowler | E21B 36/04 166/266 |
| 2002/0105429 A1 | * | 8/2002 | Donner | B61K 9/04 340/682 |
| 2010/0072123 A1 | * | 3/2010 | Haslem | G01D 5/145 210/232 |
| 2011/0156918 A1 | * | 6/2011 | Santos | G01F 23/0076 340/622 |
| 2012/0037457 A1 | * | 2/2012 | Huang | F16H 57/0405 184/7.4 |
| 2013/0034439 A1 | * | 2/2013 | Bauer | F03D 7/0224 416/1 |

FOREIGN PATENT DOCUMENTS

CN            101972949 A   *  2/2011

* cited by examiner

*Primary Examiner* — Manuel A Rivera Vargas
*Assistant Examiner* — Yaritza H Perez Bermudez
(74) *Attorney, Agent, or Firm* — Muncy, Geissler, Olds & Lowe, P.C.

(57) ABSTRACT

A lubrication detection method includes a first step is a lubricator provides an information to a processor, a second step is to detect temperature information within a predetermined time period and then to create a temperature curve and then to determine whether or not the recess in the temperature curve faces upward, and a third step of detecting a start point temperature value to form Value A, and averaging temperature values within ⅓ time period in front of the lowest point to form Value B, and average temperature values after ⅔ time period in back of the lowest point to form Value C, and determining whether or not Value B is smaller than Value A, and then determining whether or not Value B is smaller than Value C, and then generating an information of "Normal" indicative of normal lubrication.

7 Claims, 4 Drawing Sheets

LUBRICATION DETECTION METHOD FOR LINEAR MOTION SYSTEM

BACKGROUND OF THE INVENTION

1. Field of the Invention

The present invention relates to linear motion system lubrication technology and more particularly, to a lubrication detection method for use in a linear motion system.

2. Description of the Related Art

The operation of a linear module, such as ball screw, is achieved by: rotating a screw rod to move a ball nut alternatively forwards and backwards, or rotating the ball nut to move the screw rod alternatively forwards and backwards and to further achieve the effect of driving an object. During the operation of the screw rod, the balls are continuously forced into friction with the screw rod or the ball nut, Friction between the balls and the screw rod or ball nut causes the balls, the screw rod and the ball nut to wear, and also causes generation of heat, resulting in increased temperature on the linear module. If lubricating oil is not timely provided at this time, wear will become more serious. Normally, a lubricator is operated to feed an appropriate amount of lubricating oil so as to slow the foregoing friction. However, even if the lubricator is turned on to start the lubrication operation, lubrication failure can occur due to lubricator shutdown, pipeline leakage, or any factors.

The existing lubrication detection method of detecting whether or not the lubricating oil enters the linear module is achieved by installing a flowmeter in the terminal end of the oiling pipeline. Through the flowmeter, the feeding of the lubricating oil into the linear module is monitored. However, when feeding the lubricating oil through the lubricator, the pressure of the lubricating oil in the oiling pipeline and the presence of the connector between the oiling pipeline and the flowmeter greatly increase the risk of oil leakage. Further, under the condition of high linear module moving speed, it is not suitable to install a flowmeter in the linear module.

SUMMARY OF THE INVENTION

The present invention has been accomplished under the circumstances in view. It is the main object of the present invention to provide a lubrication detection method for use in a linear motion system, which eliminates the need to use a flowmeter, reduces the risk of lubricating oil leakage, and effectively achieves detection of lubrication operation when the moving speed of the linear module is increased.

To achieve this and other objects of the present invention, the lubrication detection method is used in a linear motion system comprising a linear module, a lubricator, a sensor and a processor. The linear module comprises a first movable member and a second movable member. The first movable member is kept in contact with the second movable member in such a manner that the first movable member and the second movable member are movable relative to each other. The lubricator is adapted for delivering a lubricating oil into the first movable member. The sensor is mounted on the first movable member of the linear module, and kept in contact with the first movable member. The processor is electrically coupled with the lubricator and the sensor for receiving data therefrom. The lubrication detection method comprises the steps of (1): providing an oiling information to the processor when the lubricator starts lubricating the first movable member, and continuously detecting the oiling information if the processor receives no oiling information; (2): enabling the processor to periodically detect the temperature information measured by the sensor within a predetermined time period after the processor detected the oiling information, and then enabling the processor to record the detected temperature information and to further create a temperature curve within the predetermined time period and then to determine whether or not the recess in the temperature curve faces upward, and then enabling the processor to generate an information of "Failure" indicative of a lubrication failure in case of a negative determination result; and (3): detecting a start point temperature value from the temperature information to form Value A if the recess in the temperature curve faces upward, and then calculating the average value of the temperature values within ⅓ time period in front of the lowest point of the temperature curve to form Value B, and then calculating the average value of the temperature values after ⅔ time period in back of the lowest point of the temperature curve to form Value C, and then determining whether or not Value B is smaller than Value A, and then generating the information of "Failure" if the determination result is negative, and then determining whether or not Value B is smaller than Value C if Value B is smaller than Value A, and then generating the information of "Failure" if the determination result is negative, or generating an information of "Normal" indicative of normal lubrication if the determination result is positive.

Thus, the lubrication detection method of the present invention eliminates the need to use a flowmeter and reduces the risk of lubricating oil leakage. Further, because the dimension of the sensor is smaller than a flowmeter, detection of lubrication operation can be achieved when the moving speed of the linear module is increased.

Further, the oiling information can be a high potential signal, low potential signal or pulse signal.

Preferably, the predetermined time period is selected from the range of 3 seconds to 60 seconds.

Preferably, the sensor is mounted on the first movable member of the linear module. Alternatively, the first movable member can be configured to provide a lubricator fitting. In this case, the sensor is disposed in contact with the lubricator fitting.

Preferably, the linear motion system further comprises a notification device electrically connected to the processor, and adapted for receiving the information of "Failure" and the information of "Normal". The notification device is driven on by the processor after the processor received the information of "Failure" or the information of "Normal". Further, the notification device can be a display device, lamp or buzzer.

Other advantages and features of the present invention will be fully understood by reference to the following specification in conjunction with the accompanying drawings, in which like reference signs denote like components of structure.

DETAILED DESCRIPTION OF THE INVENTION

Figure 1:
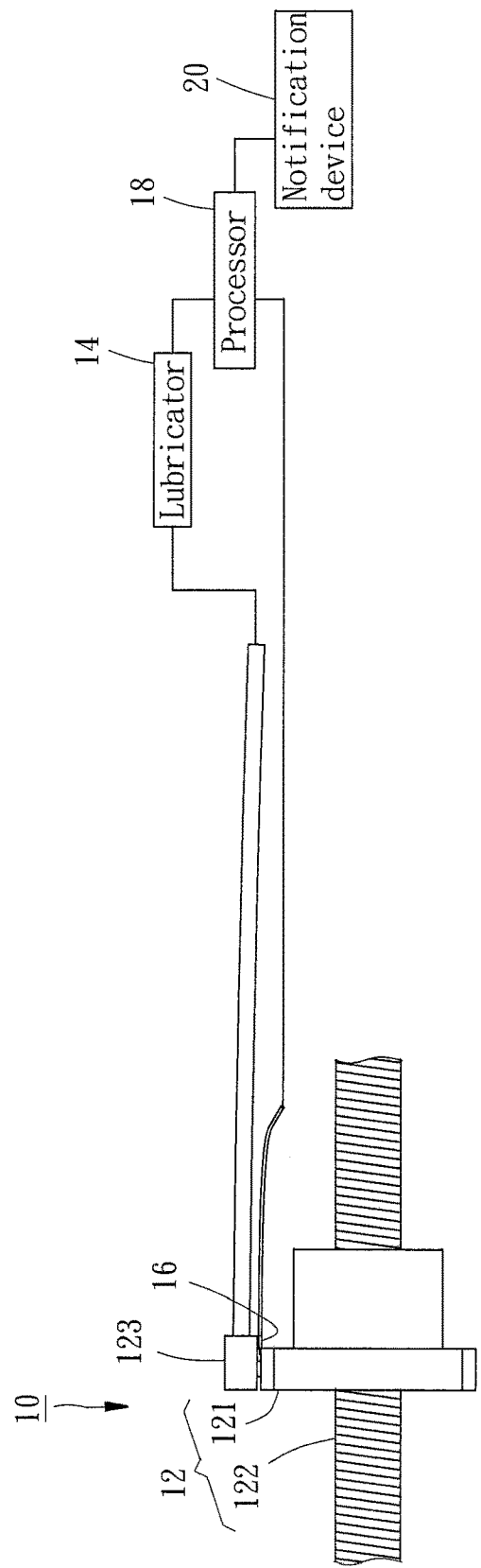
FIG. 1 is a schematic drawing illustrating the architecture of a conventional linear motion system.
Figure 2:
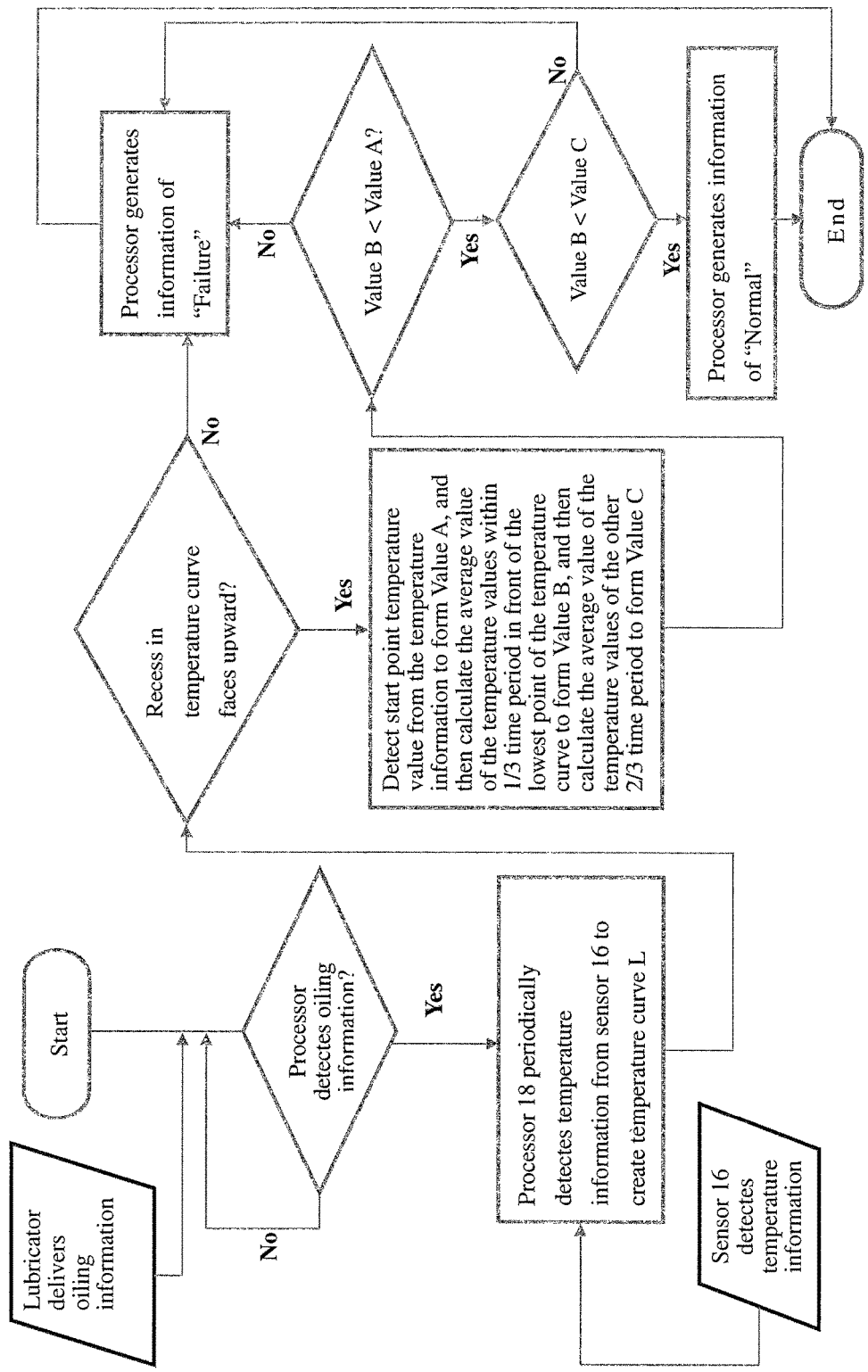
FIG. 2 is a flow block diagram of a lubrication detection method in accordance with the present invention.
Figure 3:
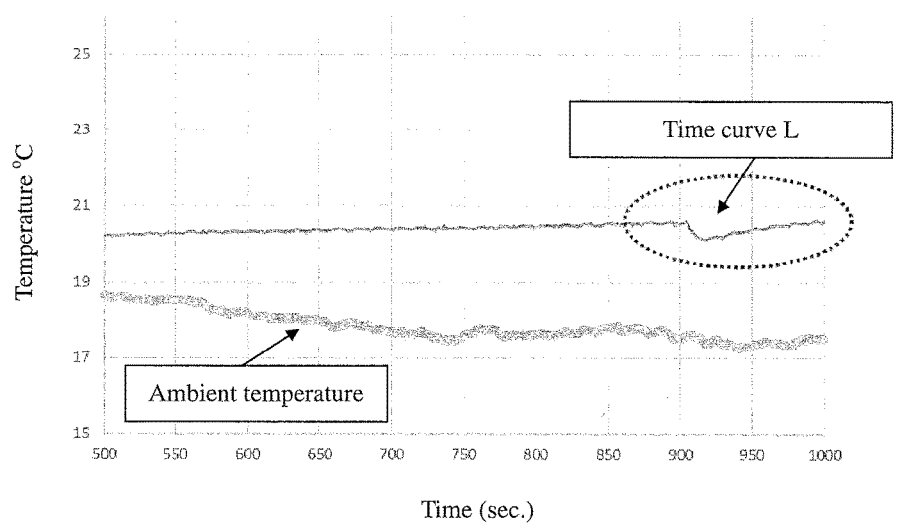
FIG. 3 is a time-temperature curve obtained according to the present invention.
Figure 4:
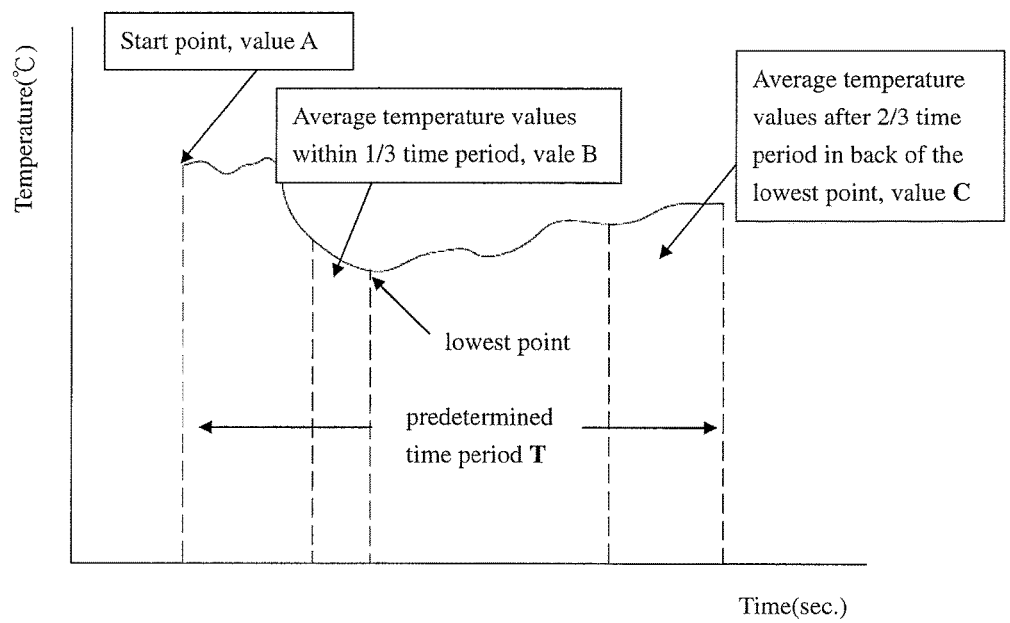
FIG. 4 is a schematic drawing illustrating the value A, value B and value C.

Referring to FIGS. 1-3, the invention provides a lubrication detection method for use in a linear motion system 10, which comprises a linear module 12, a lubricator 14, a sensor 16, and a processor 18.

The linear module 12 in this embodiment is a ball screw. However, ball screw is not a limitation. Alternatively, the linear module 12 can be a linear guideway. The linear module 12 comprises a first movable member 121, for example, ball nut or slide block, and a second movable member 122, for example, screw rod or slide rail. The first movable member 121 is kept in contact with the second movable member 122 in such a manner that the first movable member 121 and the second movable member 122 are movable relative to each other.

The lubricator 14 is adapted for delivering a lubricating oil into the first movable member 121.

The sensor 16 is mounted on the first movable member 121 of the linear module 12 and kept in contact with the first movable member 121. In the present preferred embodiment, the sensor 16 is a temperature sensor, for example, thermocouple.

The processor 18 can be a numerical controller or computer, electrically coupled with the lubricator 14 and the sensor 16 for receiving data therefrom.

The lubrication detection method is used in the linear motion system 10, comprising the steps of I~III:

Step I: When the lubricator 14 starts lubricating the first movable member 121, it provides an oiling information to the processor 18. If the processor 18 receives no oiling information, it will keep detecting the oiling information. It's worth mentioning that the oiling information can be a high potential signal, low potential signal or pulse signal.

Further, in the present preferred embodiment, the first movable member 121 is equipped with a lubricator fitting 123. The sensor 16 is kept in contact with the lubricator fitting 123. It is to be noted that the invention adopts the technique of measuring the temperature of a predetermined measuring point and determining the normality of the lubrication operation subject to temperature changes. The lubricating oil in the lubricator 14 is at room temperature. Once frictional heat is created between the first movable member 121 and the lubricator fitting 123, the temperature of the linear module 12 will be increased and will surpass the temperature of the lubricating oil. Because the temperature difference measured between the lubricating oil and the linear module 12 at the time the lubricating oil is entering the linear module 12 is larger than the temperature difference measured between the lubricating oil and the linear module 12 after the lubricating oil entered the linear module 12, the temperature measuring point is preferably at the place where the contact between the lubricating oil and the linear module 12 starts. In the present preferred embodiment, the sensor 16 is kept in contact with the lubricator fitting 123. Alternatively, the sensor 16 can be mounted on the first movable member 121 adjacent to the lubricator fitting 123.

Step II: Referring to FIG. 3 again, after the processor 18 detected the oiling information, the processor 18 periodically detects the temperature information measured by the sensor 16 within a predetermined time period T. In the present preferred embodiment, the processor 18 detects the temperature information once per second. The predetermined time period T is 50 seconds. Within this predetermined time period T (50 seconds), the processor 18 records the detected temperature information to create a temperature curve L, and then determines whether or not the recess in the temperature curve L faces upward. In case of a negative determination result (the recess in the temperature curve L does not face upward), the processor 18 generates an information of "Failure" indicative of a lubrication failure. It is to be noted that, in actual application, the predetermined time period T shall coincide with the pipeline length of the lubricator 14, so the predetermined time period T is selected from the range of 3 seconds to 60 seconds. In actual application, the effect based on the predetermined time period T shorter than three seconds or longer than 60 seconds will be inferior to that selected from the range of 3 seconds to 60 seconds.

Step III: In case of a positive result (the recess in the temperature curve L faces upward), detect a start point temperature value from the temperature information to form Value A, then calculate the average value of the temperature values within ⅓ time period in front of the lowest point of the temperature curve L to form Value B, and then calculate the average value of the temperature values after ⅔ time period in back of the lowest point of the temperature curve to form Value C.

Determine whether or not Value B is smaller than Value A, and then generate the said information of "Failure" if the determination result is negative.

If value B is smaller than Value A, determine whether or not Value B is smaller than Value C, and then generate the said information of "Failure" if the determination result is negative, or generate an information of "Normal" indicative of normal lubrication if the determination result is positive.

It is worth mentioning that the linear motion system 10 further comprises a notification device 20 electrically connected to the processor 18 and adapted for receiving the information of "Failure" and the information of "Normal". After received the information of "Failure" or the information of "Normal", drive on the notification device 20. Further, the notification device 20 can be a display device, lamp or buzzer.

In conclusion, the invention provides a lubrication detection method for use in a linear motion system, which eliminates the need to use a flowmeter and reduces the risk of lubricating oil leakage. Further, because the dimension of the sensor is smaller than a flowmeter, detection of lubrication operation can be achieved when the moving speed of the linear module is increased.

What is claimed is:

1. A lubrication detection method used in a linear motion system comprising a linear module, a lubricator, a sensor, a processor and a notification device electrically connected to said processor, said linear module comprising a first movable member and a second movable member, said first movable member being kept in contact with said second movable member in such a manner that said first movable member and said second movable member are movable relative to each other, said lubricator being adapted for delivering a lubricating oil into said first movable member, said sensor being mounted on said first movable member of said linear module and kept in contact with said first movable member, said processor being electrically coupled with said lubricator and said sensor for receiving temperature information of the linear module therefrom, the lubrication detection method comprising the steps of:

providing an oiling information to said processor when said lubricator starts lubricating said first movable member, and continuously detecting said oiling information if said processor receives no said oiling information;

enabling said processor to periodically receive the temperature information measured by said sensor within a predetermined time period during operation of the linear module after said processor detected said oiling information, and then enabling said processor to record the measured temperature information and to further create a temperature curve within said predetermined time period and then to determine whether or not a recess in said temperature curve faces upward, and then enabling said processor to generate a signal of "Failure" indicative of a lubrication failure in case of a negative determination result; and detecting a start point temperature value from said temperature information to form Value A if said recess in said temperature curve faces upward, and then calculating the average value of the temperature values within $1/3$ time period in front of the lowest point of said temperature curve to form Value B, and then calculating the average value of the temperature values after $2/3$ time period in back of the lowest point of the temperature curve to form Value C;

determining whether or not said Value B is smaller than said Value A, and then generating the signal of "Failure" if the determination result is negative; and determining whether or not said Value B is smaller than said Value C if said Value B is smaller than said Value A, and then generating the signal of "Failure" if the determination result is negative, and generating a signal of "Normal" indicative of normal lubrication if the determination result is positive; and driving the notification device by the processor during the operation of the linear module based on the signal of "Failure" to notify an operator of the lubrication failure if the signal of "Failure" is generated.

2. The lubrication detection method as claimed in claim 1, wherein said oiling information is selectively a high potential signal, low potential signal or pulse signal.

3. The lubrication detection method as claimed in claim 1, wherein said sensor is mounted on said first movable member of said linear module.

4. The lubrication detection method as claimed in claim 1, wherein said first movable member comprises a lubricator fitting; said sensor is disposed in contact with said lubricator fitting.

5. The lubrication detection method as claimed in claim 1, wherein said predetermined time period is selected from the range of 3 seconds to 60 seconds.

6. The lubrication detection method as claimed in claim 1, further comprising driving the notification device by the processor based on the signal of "Normal" to notify the operator of no lubrication failure if the signal of "Normal" is generated.

7. The lubrication detection method as claimed in claim 6, wherein said notification device is selectively a display device, lamp or buzzer.

* * * * *